United States Patent [19]

Green et al.

[11] 4,021,733

[45] May 3, 1977

[54] MOISTURE METERS

[75] Inventors: Brian John Green, Purton; Bernard Ivor Lees-Smith, Hankerton, both of England

[73] Assignee: Probe Engineering Company Limited, England

[22] Filed: Sept. 29, 1975

[21] Appl. No.: 617,726

[52] U.S. Cl. .............................. 324/61 R; 361/286
[51] Int. Cl.² ....................................... G01R 27/26
[58] Field of Search ....................... 324/61 R, 61 P; 317/246; 340/200

[56] References Cited
UNITED STATES PATENTS

| | | | |
|---|---|---|---|
| 3,009,101 | 11/1961 | Locher | 324/61 R |
| 3,025,465 | 3/1962 | Breen | 324/61 R |
| 3,039,051 | 6/1962 | Locher | 324/61 R |
| 3,109,984 | 11/1963 | Mehr | 324/61 R X |
| 3,371,568 | 3/1968 | Felix | 324/61 R X |

Primary Examiner—Stanley T. Krawczewicz
Attorney, Agent, or Firm—Young & Thompson

[57] ABSTRACT

A meter for determining the moisture content of grain or hay uses two variable capacitors. A sample of the material is compressed between the electrodes of one of the capacitors and acts as its dielectric, while the other capacitor, with a known dielectric such as air, has its capacitance simultaneously varied. The ratio of capacitances can be used to give a direct readout of the moisture content of the sample.

9 Claims, 4 Drawing Figures

MOISTURE METERS

This invention relates to moisture meters. It is particularly concerned with meters for determining the moisture content of particulate or fibrous material such as grain or hay.

With modern farming methods, it is desirable to know the moisture content of crops as this can be used to determine the optimum times of various harvesting processes. Hitherto methods of determining moisture content have been somewhat cumbersome, often involving the cutting of hay, for example, and taking samples back to a testing station with complex and expensive equipment. There are on-the-spot devices which can be used in the field, but these generally involve mixing chemicals with the sample, each being carefully weighed and measured. There are usually several quite complicated steps and time has to be allowed for chemical reactions to complete.

It is an object of this invention to provide a moisture meter which can be used in the field and which can produce almost instantaneous results without the need for mixing chemicals or carefully measuring samples.

According to the present invention there is provided a meter for determining the moisture content of particulate or fibrous material, such as grain or hay, comprising two variable capacitors, each being symmetrical to a common axis, a common control for simultaneously changing the spacing of the electrodes of each capacitor to give a linear relationship between capacitances for constant dielectrics, a known dielectric in one capacitor, means co-operating with the electrodes of the other capacitor to define a chamber adapted to receive a test sample of said material, which will serve when compressed between the electrodes as the dielectric for that capacitor, and comparator means for indicating the ratio of the capacitances.

It will be shown that this ratio can give a direct indication of the moisture content of the test sample.

Conveniently, the first dielectric is air and preferably the spacing of the electrodes is the same for each capacitor.

In a preferred embodiment said one capacitor is of annular form and surrounds the other capacitor, which is of disc-like form. Conveniently, first electrodes of each capacitor are on a first common mounting and second electrodes of each capacitor are on a second common mounting, and wherein the common control includes screwthreaded means whose relative rotation moves the mountings to vary the electrode spacing. The screw-threaded means will preferably be co-axial with the axis of symmetry.

The comparator means may include first and second operational amplifiers in series coupled by said other capacitor, said one capacitor forming a feedback circuit for the first amplifier, there being a fixed capacitor at the input to the first amplifier and another fixed capacitor forming a feedback circuit for the second amplifier. There may also be included an oscillator with an output to the input capacitor, and a phase sensitive detector which receives a second output of said oscillator and the output of the second operational amplifier, said detector being adapted, or being switchable between two states, to respond solely to the capacitive or resistive element of the sample impedance.

For a better understanding of the invention some constructional forms will now be described by way of example with reference to the accompanying drawings, in which.

Figure 1:
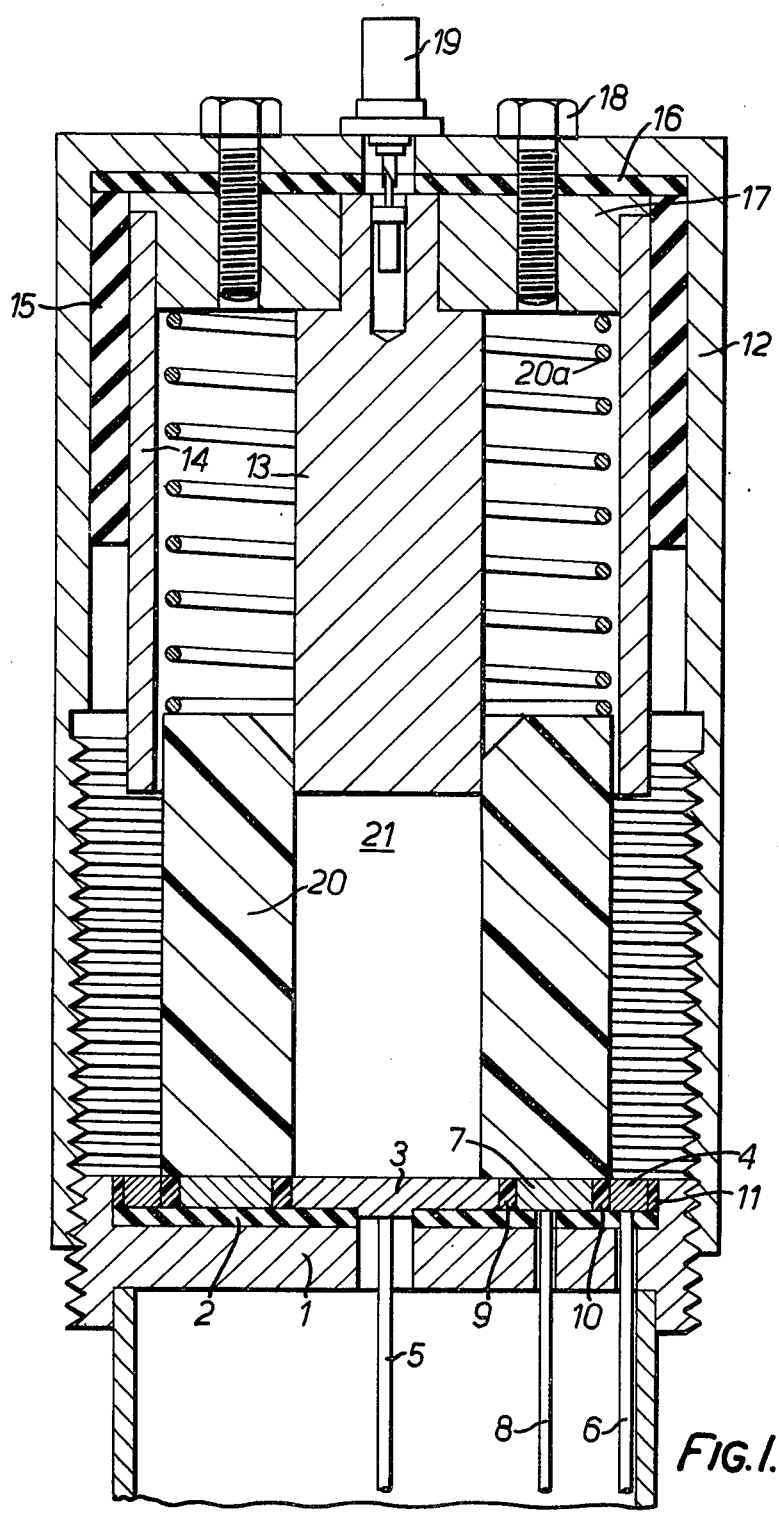
FIG. 1 is an axial section of the sample receiving structure of a moisture meter according to the invention.

The structure of FIG. 1 comprises a circular base 1 whose cylindrical outer periphery is screw threaded and which carries, recessed into its upper face, an insulating disc 2 on which are mounted concentric electrodes 3 and 4. The central electrode 3 is of disc-like form and has a lead 5 extending through the centre of the base 1. The electrode 4 is annular and has a lead 6 also extending through the base 1. The electrodes 3 and 4 have radially interposed between them an annular guard ring 7 which is normally held at earth potential through a lead 8 and which is electrically and mechanically separated from the electrodes 3 and 4 by resin fillings 9 and 10. A further annular resin filling 11 separates the electrode 4 from the outer edge portion of the base 1. The upper surfaces of the electrodes the guard ring and the resin fillings are all co-planar.

A cylindrical outer casing 12 is closed at its upper end and is internally screw threaded at its open lower end to engage the screw threading on the base 1. Coaxially housed within the casing 12 is a piston 13 whose lower face, as viewed in the figure, is of equal area to annd opposes the electrode 3, and an outer shell 14 whose annular lower end face opposes and substantially corresponds to the outer electrode 4. The shell 14 is separated from the inner wall of the casing 12 by an insulating sleeve 15 and an insulating plate 16 is interposed between the closed end of the casing 12 and a block 17 of electrically conductive material to which the piston 13 and shell 14 are rigidly secured to form a single electrode assembly. This is secured to the casing 12 by nylon bolts 18. The lead to the electrode assemblyformed by elements 13, 14, and 17 is through a co-axial cable socket 19 at the centre of the end face of the casing 12. There is also provided a cylinder 20 of insulating material, such as glass reinforced nylon, in which the piston 13 is a sliding fit. A spring 20a is housed between the electrodes 13 and 14 and reacts against the element 17 to urge the cylinder downwards. When assembled as shown, this cylinder, the end face of the piston and the electrode 3 form a compression chamber 21 for a test sample. The remainder of the electrical circuitry, an indicator and batteries to power the devive may be housed in any convenient manner below the base 1.

For use, the casing 12 is removed and the sample to be tested is placed within the cylinder 20 and trimmed off as necessary. There is no need for a carefully measured sample. The cylinder is centred on the base and the casing 12 is then reassembled therewith and screwed down so that the piston 13 compresses the sample in the chamber 21. The casing 12 is tightened by hand until the sample is substantially fully compressed, in which case there may be as little as 2% air in it. This is insufficient to give any significant reading error. The fit of the piston 13 within the cylinder 20 and the spring loading of the cylinder will permit air to escape as the casing is screwed down, and the casing itself will be vented to avoid compressing air. By a circuit such as that to be described later, a comparison of the capacitance of the capacitor formed by the electrode 3 and the piston 13 and that of the capacitor formed by the electrode 4 and the shell 14 is made. This gives a direct reading of the moisture content of the sample which acts as a dielectric, whose constant is directly related to that moisture content.

Figure 2:
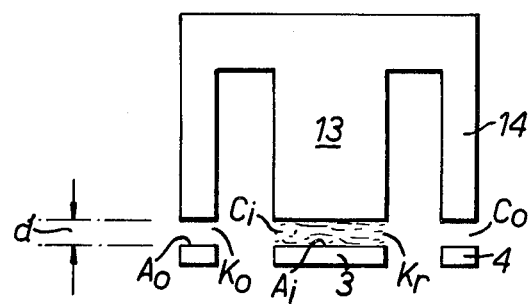
FIG. 2 is a diagram for use in explaining the relationship between capacitances of said structure.

Referring now to FIG. 2 there is shown in simplified form the electrode arrangement, using the same references. In the following, $K_o$ refers to the permittivity of free air which forms the dielectric of the outer capacitor, $K_r$ to the relative permittivity of the sample (which is directly related to the moisture content), $d$ to the electrode spacing (the same for each capacitor), $A_i$ to the area of the inner electrode, $A_o$ to that of the outer, $C_i$ to the capacitance of the inner capacitor and $C_o$ to that of the outer.

Now
$$C_o = (K_o A_o/d)$$
and
$$C_i = (K_o K_r A_i/d)$$
Therefore
$$(C_i/C_o) = (K_r A_i/A_o)$$

But since $A_i$ and $A_o$ are mechanical constants
$$(C_i/C_o) \propto K_r$$

Figure 3:
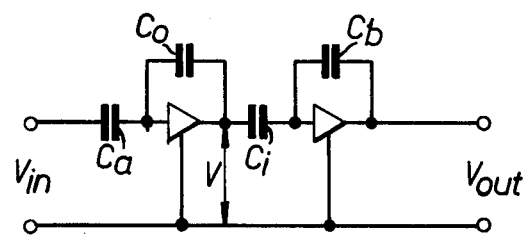
FIG. 3 is a circuit diagram of a comparator.

There are many circuits that can be employed to compare capacitances and give an output that corresponds to their ratio, but preferred circuit is shown in FIG. 3. This has two operational amplifiers of very high gain and the arrangement is such that the effects of any stray capacitances at input or output are virtually eliminated. $C_o$ provides the feedback of the first amplifier and $C_i$ the coupling between the two amplifiers. The input voltage $V_{in}$ is alternating.

With this circuit $$V_{out}/1/sC_b = V/1/sC_i$$

where s is the Heaviside transform
$$V_{out} s C_b = V s C_i$$

Similarly
$$V_{in} s C_a = V s C_o$$

And hence
$$V_{in} s C_a = (sC_o \, V_{out} sC_b/sC_i)$$

$$\therefore \quad \frac{V_{out}}{V_{in}} = \frac{C_a}{C_b} \times \frac{C_i}{C_o}$$

Now with $C_a$ and $C_b$ fixed capacitors $$(V_{out}/V_{in}) \propto (C_i/C_o) \propto K_r$$

If $V_{in}$ is of constant amplitude and frequency $$V_{out} \propto K_r$$

Alternatively $V_{in}$ may be allowed to vary and $V_o$ kept constant, in which case $$V_{in} \propto 1/K_r$$

In a third method of using this circuit, the gain ($V_{out}/V_{in}$) may be measured to give an indication of $K_r$.

Figure 4:
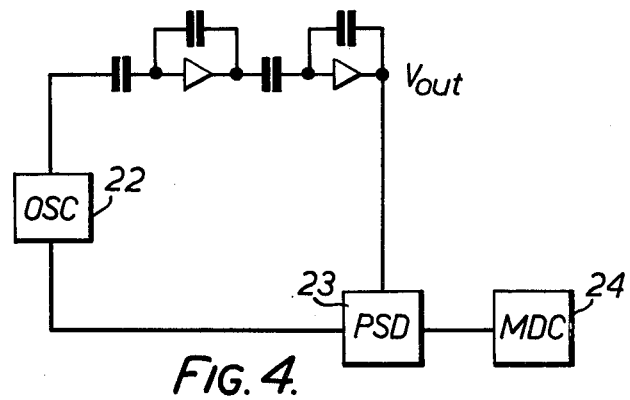
FIG. 4 is a circuit diagram of a further comparator circuit.

FIG. 4 shows a development of this circuit, whereby in-phase components that may be present in the impedance provided by the sample (which can be considered in the chamber 21 as a capacitor and resistor in parallel) can be rejected. The oscillator 22 which feeds the circuit of FIG. 4 also has an output to a phase sensitive detector 23. The latter also receives $V_{out}$ from the part of the circuit corresponding to FIG. 3 and may be so adapted that a meter drive circuit 24 responds only to the capacitive element of the complex impedance of the sample.

The detector 23 may also be switched to receive a 90° phase shifted osciallation from 22, in which case only the resistive element of the complex impedance will be measured.

We claim:

1. A meter for determining the moisture content of particulate or fibrous material, such as grain or hay, comprising two variable capacitors, each being symmetrical to a common axis, a common control for simultaneously changing the spacing of the electrodes of each capacitor to give a linear relationship between capacitances for constant dielectrics, a known dielectric in one capacitor, means co-operating with the electrodes of the other capacitor to define a chamber adapted to receive a test sample of said material, which will serve when compressed between the electrodes as the dielectric for that capacitor, and comparator means for indicating the ratio of the capacitances.

2. A meter as claimed in claim 1, wherein said known dielectric is air.

3. A meter as claimed in claim 1, wherein the electrode spacing is the same for each capacitor.

4. A meter as claimed in claim 3, wherein said one capacitor is of annular form, surrounding said other capacitor, which is of disc like form.

5. A meter as claimed in claim 1, wherein first electrodes of each capacitor are on a first common mounting and second electrodes of each capacitor are on a second common mounting, and wherein the common control includes screw-threaded means whose relative rotation moves the mountings to vary the electrode spacing.

6. A meter as claimed in claim 5, wherein said screw-threaded means are co-axial with the axis of symmetry.

7. A meter as claimed in claim 1 wherein the comparator means includes first and second operational amplifiers in series coupled by said other capacitor, said one capacitor forming a feedback circuit for the first amplifier, there being a fixed capacitor at the input to the first amplifier and another fixed capacitor forming a feedback circuit for the second amplifier.

8. A meter as claimed in claim 7, wherein the comparator means includes an oscillator with an output to the input capacitor.

9. A meter as claimed in claim 8, including a phase sensitive detector which receives a second output of said oscillator and the output of the second operational amplifier, said detector being adapted, or being switchable between two states, to respond solely to the capacitive or resistive element of the sample impedance.

* * * * *